United States Patent [19]

Kamen

[11] Patent Number: 4,648,872

[45] Date of Patent: Mar. 10, 1987

[54] VOLUMETRIC PUMP WITH REPLACEABLE RESERVOIR ASSEMBLY

[76] Inventor: Dean L. Kamen, 46 Gage Rd., Bedford, N.H. 03102

[21] Appl. No.: 551,851

[22] Filed: Nov. 15, 1983

[51] Int. Cl.$^4$ ............................................. A61M 37/00
[52] U.S. Cl. .................... 604/155; 604/211; 604/224; 604/228; 604/245; 128/DIG. 12; 222/390
[58] Field of Search ............... 604/155, 65, 67, 118, 604/151, 152, 154, 208, 211, 213, 218, 224, 228, 230, 245, 110; 128/DIG. 12; 222/390

[56] References Cited

U.S. PATENT DOCUMENTS

| | | | |
|---|---|---|---|
| 996,128 | 6/1911 | Payne et al. | |
| 2,602,446 | 8/1952 | Glass et al. | 128/218 |
| 2,627,270 | 2/1953 | Glass | 604/155 |
| 2,627,999 | 2/1953 | Swan | 222/390 |
| 2,725,877 | 12/1955 | Reiter et al. | 604/224 |
| 2,734,504 | 2/1956 | Crescas et al. | 604/155 |
| 3,155,090 | 11/1964 | Holter | 128/2 |
| 3,156,236 | 11/1964 | Williamson | 128/2.05 |
| 3,395,704 | 8/1960 | Frey et al. | 604/154 |
| 3,456,649 | 7/1969 | Jewett | 128/214 |
| 3,623,474 | 11/1971 | Hellman et al. | 128/2 R |
| 3,631,847 | 1/1972 | Hobbs | 128/2 R |
| 3,701,345 | 10/1972 | Hellman et al. | 128/2 R |
| 3,771,694 | 11/1973 | Kaminski | 128/DIG. 13 |
| 3,790,048 | 2/1974 | Luciano et al. | 604/211 |
| 3,811,442 | 5/1974 | Maroth | 128/218 R |
| 3,812,843 | 5/1974 | Wootten et al. | 128/2 R |
| 3,858,581 | 1/1975 | Kamen | 128/218 A |
| 3,880,138 | 4/1975 | Wootten et al. | 128/2 A |
| 3,886,938 | 6/1975 | Szabo et al. | 128/218 A |
| 4,059,110 | 11/1977 | Wuthrich et al. | 128/218 A |
| 4,073,321 | 2/1978 | Moskowitz | 604/208 |
| 4,108,177 | 8/1978 | Pistor | 604/155 |
| 4,126,132 | 11/1978 | Portner et al. | 128/214 F |
| 4,142,524 | 3/1979 | Jassawalla et al. | 128/214 F |
| 4,150,672 | 4/1979 | Whitney et al. | 128/214 F |
| 4,191,187 | 3/1980 | Wright | 128/218 A |
| 4,258,866 | 3/1981 | Bergman | 222/390 |
| 4,269,185 | 5/1981 | Whitney et al. | 128/214 F |
| 4,300,554 | 11/1981 | Hessberg et al. | 128/218 A |
| 4,320,757 | 3/1982 | Whitney et al. | 128/214 F |
| 4,326,517 | 4/1982 | Whitney et al. | 128/214 F |
| 4,342,311 | 8/1982 | Whitney et al. | 128/214 F |
| 4,367,738 | 1/1983 | Legendre et al. | 604/110 |
| 4,391,272 | 7/1983 | Staempfli | 604/110 |
| 4,399,712 | 8/1983 | Oshikubo et al. | 604/155 |
| 4,465,475 | 8/1984 | Madorf et al. | 604/155 |
| 4,493,704 | 1/1985 | Beard et al. | 604/154 |

*Primary Examiner*—Stephen C. Pellegrino
*Assistant Examiner*—Mark Rooney
*Attorney, Agent, or Firm*—Bromberg, Sunstein & McGregor

[57] ABSTRACT

An infusion pump has a removable reservoir including a piston and drive member. The drive member is an internally threaded elongated portion of the piston. A motor rotates a short drive screw, which engages the threads of the drive member to displace the piston in the reservoir. In one embodiment the piston is attached to the drive member by a severable central stem which breaks away to allow engagement with the drive screw. With the stem severed, the piston cannot be retracted, or the reservoir refilled. Other safety features are shown for locking the displaced piston in the reservoir. A digital metering system has a safety circuit to prevent dangerous failure modes of the rotation sensor and motor drive systems.

7 Claims, 17 Drawing Figures

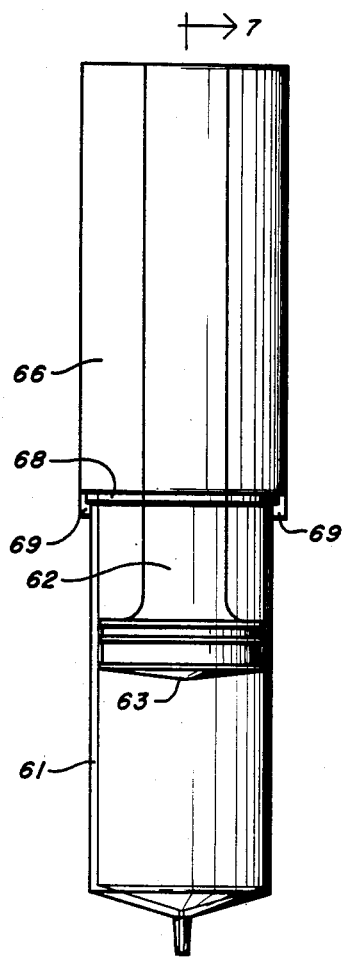
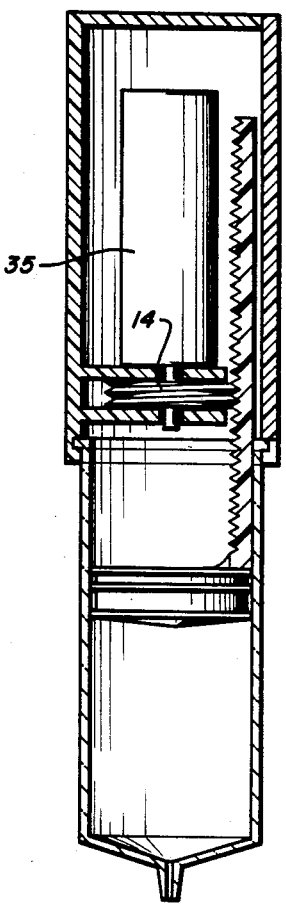
FIG. 6  FIG. 7
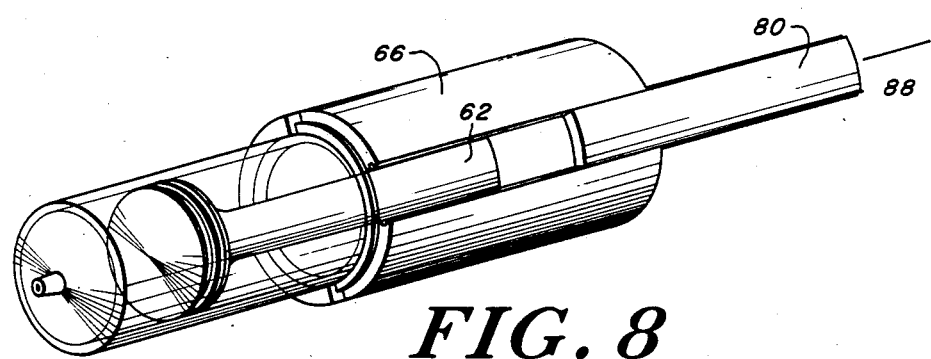
FIG. 8

VOLUMETRIC PUMP WITH REPLACEABLE RESERVOIR ASSEMBLY

TECHNICAL FIELD

This invention relates to medical infusion pumps and more particularly pumps capable of home use by ambulatory patients and pumps having built in controls for sustained or periodic infusions over a substantial time.

BACKGROUND ART

Much interest has arisen in recent years in the development of medical infusion pumps capable of relatively continuous operation and also in the development of infusion pumps having the ability to administer precisely controlled volumes of fluid at preselected intervals. Unlike the case with a parenteral fluid administration apparatus, which typically operates by gravity flow from a relatively large reservoir of fluid, medication infusion generally involves administration of small dosages so as to achieve a prescribed optimum level of medication in the bloodstream of the patient. Due to differences in the rates of metabolism of, or elimination of, various medicines, the attainment of precise bloodstream medication levels is usually achieved by the periodic administration of a dosage of medication, where determination of the precise dosage and the correct interval between doses will depend on the particular medication involved as well as criteria peculiar to the patient. Such repeated administration of medicines can be difficult to achieve because of erratic communications with, or supervening demands on, hospital nursing staff; moreover repeatedly giving a patient injections can be traumatic. Thus emphasis has grown on developing versatile medical infusion pumps to automatically administer a sustained sequence or rate of infusions. Pumps of several types are known in the prior art. One species of pump involves rather massive mechanical elements for the pump and dosage setting device so as to give the very precisely controlled sequence of high pressure infusions necessary for radiography. Such devices are disclosed in U.S. Pat. Nos. 3,701,345 and 3,812,843, among others.

Another, general purpose, species of pump utilizes a motor or clock drive to power a pushing mechanism, using a leadscrew or rack, for moving a plunger arrangement. Examples of such devices are my medication injection device disclosed in U.S. Pat. No. 3,858,581, or that of U.S. Pat. No. 4,059,110. Such devices are more compact and are reasonably well adapted for use as bedside periodic infusion devices in a hospital setting. However these devices tend to be somewhat bulky and, for this reason, are less than optimal for use on an ambulatory patient. Each of the prior art devices also suffers from a looseness in its mechanical drive components which requires close attention when setting up the initial pumping operation to ensure that the device actually pumps a full dose during the first duty cycle of its activation. Additionally each of the prior art devices has a rather complex mechanical structure, introducing significant inertial and frictional factors affecting the ease and cost of maintaining the units in reliable operating condition over extended times, and making them unsuitable for battery powered operation.

BRIEF DESCRIPTION OF THE INVENTION

The present invention overcomes the foregoing limitations by providing a simplified mechanical structure for a pump including a reservoir, piston and drive member, in which the drive member may be internally threaded for a substantial length. A relatively short drive screw, which may be motor driven, engages the drive member to propel the piston in the reservoir. By using a piston drive member in which the skirt is omitted on one side, it is possible to place the motor and drive screw substantially within the extended piston member body, realizing a substantial reduction in space requirements. Additionally, such a structure requires no drive member journals, and dispenses with the cumbersome rack or leadscrew characteristic of prior art devices. There may result a pump structure with minimal mass, minimal frictional losses or mechanical inefficiency, and no mechanical backlash. In a preferred embodiment the reservoir, piston, and drive member may be an assembly that can be removed from the pump. In one preferred embodiment, interlocking detents on the piston and reservoir walls may be used to prevent withdrawal or reuse of the reservoir assembly or components after use. In another preferred embodiment, a shearable stem, which may be integrally formed with the piston face, holds the piston and drive member together for setting up or bleeding the pump. The stem then is sheared off by twisting so that the piston face floats free, preventing re-use of the reservoir assembly. The invention is well adapted for use with battery powered drive, and microprocessor chip control programming means, for dependable use with small power requirements in hospital bedside or ambulatory outpatient settings. These and other features of the invention will become apparent by reference to the drawings.

BRIEF DESCRIPTION OF THE DRAWINGS

FIG. 6 shows a large volume embodiment adapted for sustained bedside infusion.

FIG. 7 shows a section along line 7—7 of FIG. 6, showing the motor and drive.

FIG. 8 shows the embodiment of FIG. 6 having the retaining slide cover.

DETAILED DESCRIPTION OF THE INVENTION

Figure 1A:
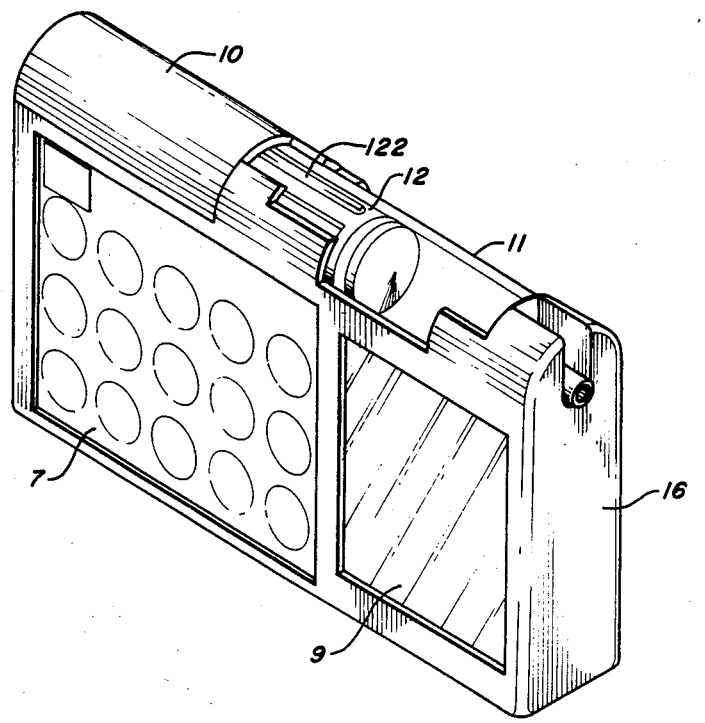
FIG. 1A shows a perspective view of a programmable microprocessor-controlled embodiment of the invention.

FIG. 1A shows a perspective view of a complete infusion pump according the present invention, in which a housing 16, containing a power supply and microprocessor control circuity, accomodates a motorized drive unit and a disposable piston/reservoir assembly in its upper portion. A keyboard 7, preferably of an impermeable, e.g. membrane-type, construction is used to enter program information to set a schedule of amounts and timing of medication doses. A display 9 is used to display the instrument mode, to give instructions for data entry, and to signal certain operator correctable steps and alarm states. In the upper portion of the housing is mounted a reservoir 11 with a centrally disposed elongated piston member 12. The reservoir 11 is secured at one end by a gentle snap fit within opposing portions of a yoke 15 formed by the housing body. (A single side of yoke 15 is shown in this figure.) At the other end of the reservoir is an axially-sliding cover portion 10 of the housing which overlies the end of the reservoir 11 and bears against the longitudinal portion of piston member 12 to align it. To minimize friction against the piston member 12 as it slides within the reservoir 11, there is provided a protuding longitudinal ridge 122 comprising the area of contact between the piston member and the reservoir 11 and sliding cover 10.

Figure 1B:
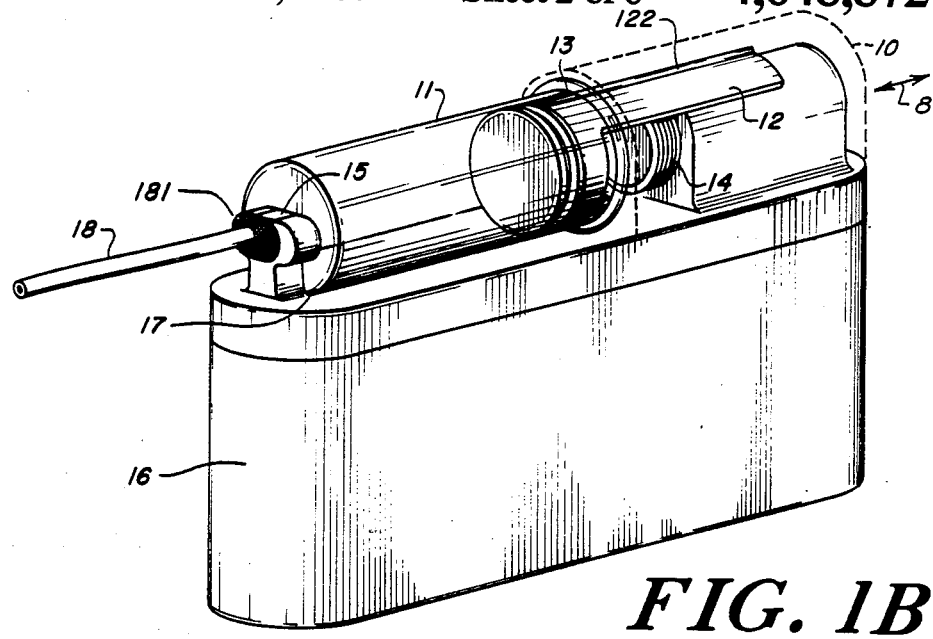
FIG. 1B shows a perspective view of an embodiment similar to that of FIG. 1A.

FIG. 1B shows a perspective view of a complete infusion unit similar to the embodiment of FIG. 1A and viewed from the opposite side. A reservoir 11, which may be graduated along its surface, fits into a recess 17 in the unit's housing 16 and is retained by the yoke 15 which varies only slightly from the yoke shown in FIG. 1A. The reservoir 11 is substantially in the form of a hollow cylinder, and yoke 15 is positioned so as to retain the reservoir in axial alignment. It has been found that the use of the split yoke 15 permits convenient insertion of the reservoir 11 into recess 17. This yoke is located to position the outlet nipple, shown at 29 in FIG. 2, leaving space for the attachment of a connector 181 and infusion tube 18, both of which are of a conventional design. Also shown in FIG. 1B are the piston member 12, an elongated member with a substantially circular head 13 for hermetically displacing the fluid in the reservoir 11 when driven by the rotating screw drive 14 on the shaft of the drive motor (not visible). As shown, the housing 16 removably holds the reservoir 11 and piston member 12 as a unit. The circular piston head 13 displaces fluid in the reservoir upon axial motion of the piston member. The rearward portion of the piston member is shaped like a longitudinal segment of cylinder as shown and is preferably internally threaded so that it may be inserted into a position of engagement with drive screw 14. Drive screw 14 is a finely threaded screw gear, of a diameter to mesh with the internal threads of the piston member 12.

In the embodiment shown, all of the mechanical elements of the pump and drive are housed in the top portion of the housing 16 and the remainder of housing 16 serves to hold a battery or rechargeable power pack and a microprocessor control and rate selection means for the device. A cover 10, shown in phantom, slides in the direction of axis 8 so as to hold the piston member 12 in engagement with the drive screw after the reservoir assembly is inserted in the housing. Alternatively, the cover 10 may be an integral fixed part of the housing 16, and provided with a slot on the side thereof and longitudinally disposed along axis 8; the slot would be sufficient in size to permit insertion of the piston member 12 when the piston-reservoir assembly is first loaded into the motor assembly. After the insertion of the piston member 12 into the slot, the piston member 12 is rotated about axis 8 until the member 12 assumes operating position underneath the cover, where the member 12 may be retained by one or more nubs protruding toward axis 8 from the inside of the cover near the slot. In this manner the cover holds the piston in engagement with the drive screw.

Figure 2:
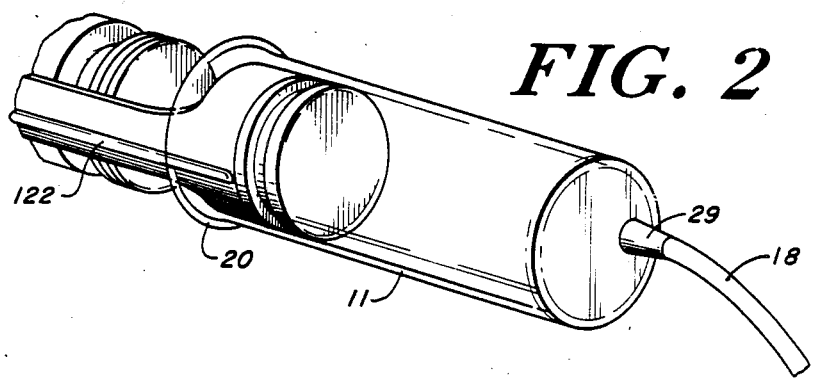
FIG. 2 shows details of a disposable reservoir, in accordance with the present invention, with the piston and drive member withdrawn.

FIG. 2 shows the reservoir 11, with its outlet nipple 29. The outlet nipple may be of any conventional shape such as a taper or bayonet lock, for attachment of a sterile connector fitting 181 and infusion tube 18. When used to center the reservoir with respect to a retaining stop as shown at 15 in FIG. 1B the nipple must be of sufficient length so that the stop 15 does not interfere with attachment of the connector fitting.

At the other end of the reservoir is the rear edge 20 of the circular opening constituting the end of the reservoir chamber. The present device is intended for use in administering infusions over extended periods of time thus entailing some likelihood of contamination, or incubation of bacterial contaminants. For this reason, it is necessary to guard against misuse, particularly the possibility that reservoir units may be removed and refilled with medication. Such refilling is poor medical practice, and would pose a substantial risk of introducing pyrogenic, infectious or otherwise toxic contaminants into the infusion fluid.

Figure 2A:
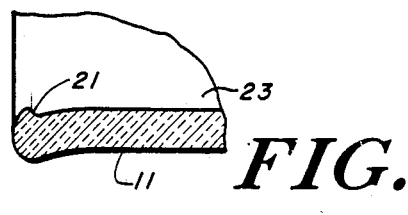
FIGS. 2A, 2B and 2C show various embodiments of a reservoir safety retaining feature utilizing a lip, barb, or groove.
Figure 2B:
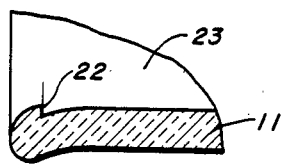
Figure 2C:
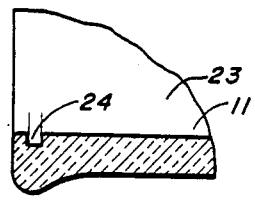

Accordingly in one preferred embodiment of this invention, a safety feature has been incorporated to prevent withdrawal of the piston and refilling of the reservoir. This safety feature includes a modification to the inner surface contour of the reservoir adjacent to the rear edge 20 of the reservoir, together with a mating modification to the distal end of the piston member. Such modifications to the reservoir assembly are shown in cross-section in FIGS. 2A, 2B, and 2C, and may include a lip 21, a barb 22, or a groove 24 located to engage the piston member and prevent its withdrawal after use. The piston member has a corresponding barb 32 shown in FIG. 3A projecting radially outward from its distal end which engages the mating portion of the reservoir wall for causing the piston to be locked into the reservoir upon full insertion. The piston member also has a rounded shoulder 33 preferably extending along each edge of the piston member, to prevent gripping the member which could defeat the safety lock. It has been found that the lip 21 or barb 22 of the reservoir need not protrude more than a few thousandths of an inch above the interior face 23 of the reservoir chamber to be effective, and thus need introduce no unreasonable frictional drag upon the piston member. Frictional drag may be altogether eliminated by use of the groove 24 and barb 32 embodiment of the safety interlock.

Figure 3:
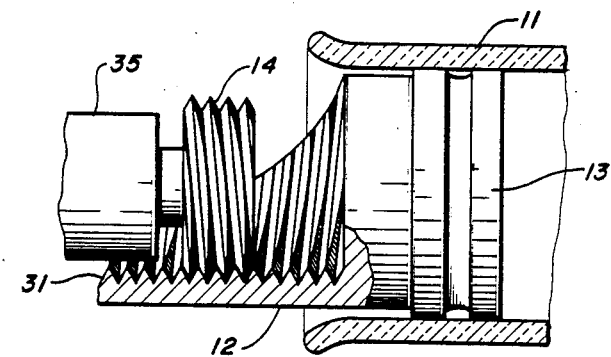
FIG. 3 shows a side view of the piston and drive member, showing the placement of the motor and drivescrew within its contours.
Figure 3A:
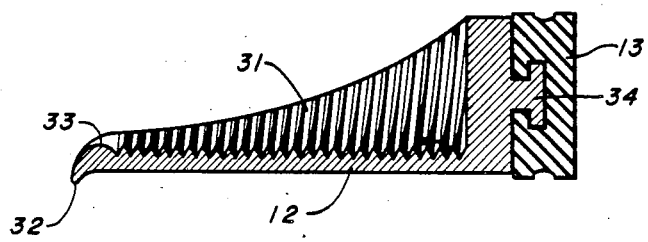
FIG. 3A shows a cross-sectional view of the piston member and safety barb.
Figure 3B:
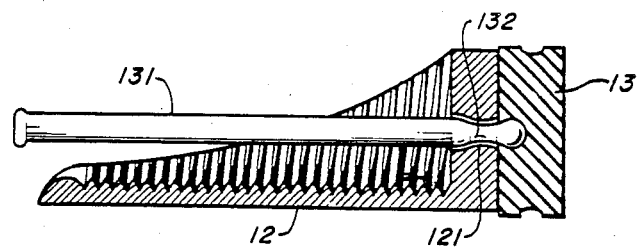
FIG. 3B shows a cross-sectional view of the piston member and the breakaway safety stem.

A further preferred embodiment is shown in FIG. 3B. (FIGS. 3 and 3A are discussed below.) In the embodiment of FIG. 3B, piston face 13 is attached to a safety stem 131, which may be integrally formed with face 13, extending through aperture 121 in piston member 12, and holding face 13 to member 12. Safety stem 131 is capable of transmitting force in either direction along its length, and accordingly to set up and bleed a reservoir it is only necessary to push or pull on stem 131 as for a conventional syringe. However, with stem 131 intact, it is not possible to place the reservoir into the housing 16 or into engagement with the motor drive gear 14. Accordingly, to mount the assembly for operation, the stem is twisted, breaking off at a narrowed stress point 132, thus removing the obstacle to motor engagement. With the stem thus removed, the face 13 is no longer attached to the piston body 12. It will advance when driven by the piston member, but will remain within the reservoir and will not retract when member 12 is withdrawn. Face 13 may contain a polygonal recess fitted over a corresponding polygonal protrusion of body 12 to prevent face 13 from turning as the stem is twisted to break it away, thus facilitating the breaking away of the safety stem.

FIG. 3A shows a longitudinal cross section of one embodiment of the piston member 12, in which 34 is a nub integrally formed with piston member 12 for retaining the front face 13. Internal screw threads 31 extend the length of the inside face of the piston member back from the front face, culminating in a rounded shoulder, 33 visible at the distal edge. On the exterior face of the piston member 12 precisely at the distal end thereof is a slight protrusion 32 which engages the corresponding lip 21, barb 22 or groove 24 shown at FIGS. 2A, 2B, or 2C when the piston has been fully displaced into the reservoir 11, thus preventing removal of the piston or refilling of the reservoir. In this regard the shoulder 33 further discourages gripping of the piston, to safeguard against removal.

Referring now to FIG. 3, there is shown in side view the piston member 12 including the front face 13, which is shown somewhat occluded by the surrounding reservoir 11. Piston face 13 may be a soft neoprene or similar FDA-approved compound, such as is commonly used in the plunger of disposable syringes, which is fitted over a ridged end or bulbous nub at the end of the piston member so as to be controllably moveable thereby. The precise mode of attachment is well known in the art, and accordingly no particular detail of that structure is shown. The portion of the piston member 12 which is immediately behind the soft front face 13 is substantially circular in cross-section, tapering to a long narrow body, which is shaped substantially like a segment of a cylinder of roughly constant thickness, threaded on the inside. The threads 31 are shown in cross-section. The precise shape of the long cylindrical segment is not critical so long as the exterior approximately conforms to the inner contour of the reservoir and the segment is not unduly wide or narrow. For the long portion of the piston member, a width of between 1/16 and 3/8 of an inch has been found to be practical, as it provides good engagement with the drive gear 14, has adequate rigidity and compressive strength to transmit the drive force, and is thin enough to avoid causing frictionally induced motion from the turning of the drive screw gear 14.

Also shown in FIG. 3 is the screw gear 14 attached to the shaft of motor 35. As shown in FIG. 3 the motor has its principal cross-sectional dimension less than the diameter of the screw gear, so that it fits entirely within the cylindrical region formed by rotating the piston member 12 about the common central axis of the reservoir/piston assembly. An electromagnetic motor having an integral high-ratio gear reduction unit coaxially mounted in a common housing between the motor and drive gear has been used. This allows the motor 35 to drive the piston member 12 directly via the drive screw gear 14 without requiring other shafts, gears, pulleys, journals or other mechanical coupling or supporting elements in housing 16, resulting in a reduction of both inertial load and frictional losses as compared to conventional pumps. The screw gear drive may be of any appropriate pitch with the choice of pitch dependent on the cross-sectional area of the reservoir, the desired delivery rates and infusion pressures, the available motor speed and torque output and the desired operational cycles.

In constructing the screw drive, the thread profile of the screw gear in relation to the threads of the inner surface of the piston member is of some importance. In order to reduce backlash in the drive assembly, it is useful either to provide sharp peaks on the drive gear threads, so that the gear bites somewhat into the trenches of the threads of the piston member, or to provide a slight convexity or preloading in the face of the threads of either the drive gear or the piston member.

The operative metering principle involved in the control system of the present pump is that rotations of the drive screw 14 are directly proportional to the linear displacement of piston, hence to the volume of medicine delivered. The automatic control system for the present pump utilizes an internal light source which is reflected by a segmented optical disc connected to the drive train and detected by a photodetector so as to generate, in a manner known in the art, pulses representative of drive screw rotation. The control system operates the pump, starting at a predetermined time, and continuing until a predetermined number of pulses have been generated.

Because the reservoir 11 holds sufficient medication for many hours or days of therapy, extreme precautions must be taken to assure that the pumps do not have faults which might result in a continuous pumping failure mode. This might occur for instance if the light source failed to turn on, or burned out, so that no reflected pulses signalled the continued operation of the pump. To prevent the occurrence of such dangerous events, a novel arrangement is used in the drive system of the pump. Specifically the light and drive motor are wired in series or otherwise arranged so that both necessarily receive power if and only if the other is receiving and drawing power. In addition, condition sensing and power enabling circuitry are provided to further assure the device will shut down in the event a drive-sensing component fails. In particular a second photodetector is provided to detect direct (as opposed to reflected) light from the internal light source; in the event that the second photodetector fails to detect light from the internal light source, the circuitry causes power to be removed from light-drive motor combination. With this approach the motor is powered and medicine is delivered to the patient only if the motor, the light, and the turn-counting mechanism are all functioning. This circuit eliminates the dangers of undetected motor jamming or lamp burnout. This peculiar arrangement of the operating components with the logic and condition sensors necessarily assures that none of the permutations of component failure can result in a dangerous operating condition, but merely in shut-down of the device.

The foregoing discussion is not restricted to a rotation sensing system using reflected light, and it would be obvious to one skilled in the art to construct a corresponding safety system for use in a rotation sensor employing a slotted disc and a transmitted beam of light. Accordingly the terms "reflected" or "reflecting" shall include "transmitted" or "transmitting" when used herein and in the claims. The precise details of the signal generation and detection also may be put into practice using a variety of components in a manner well known in the art.

Figure 4:
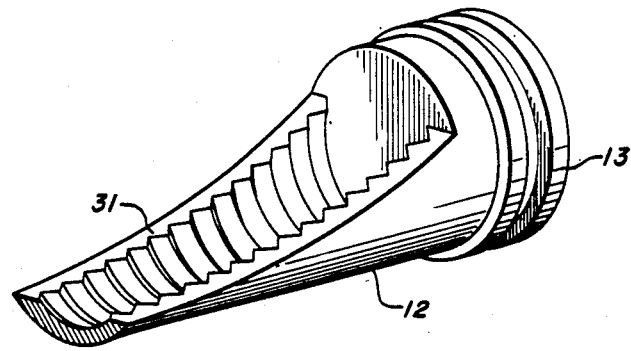
FIG. 4 shows a perspective view of the piston member, skirt profile and drive engagement threads.

Turning now to FIG. 4, there is shown the piston member generally at 12 having internal threads 31 disposed along the length of the piston skirt, the portion of piston member 12 which extends laterally outward from piston head 13 and receives rotating screw gear 14. By engagement with the short rotating screw gear 14 the threads are operative to drive the piston a distance equal to the length of the threads 31. Because the piston skirt must slide laterally into engagement with the drive screw, the skirt comprises not much more, and preferably less, than a semicircumferential portion of the cylindrical surface. In fact, since the piston skirt is used to transmit a linearly-directed drive force, shear forces are negligible; and because the piston head 13 is joined to the skirt portion along an arcuate edge, the skirt may safely be quite narrow.

Figure 5A:
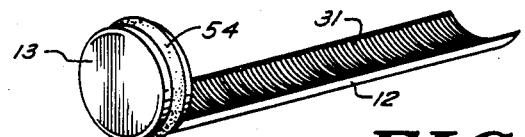
FIGS. 5A, 5B and 5C show different embodiments of the piston face adapted to provide a fluid seal.
Figure 5B:
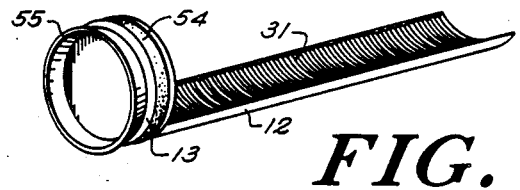
Figure 5C:
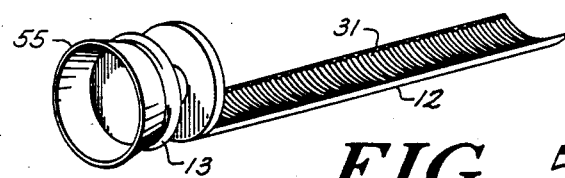

Such a drive member 12, having a narrow skirt, is shown in FIGS. 5A, 5B and 5C, each of which shows an alternative embodiment of the piston face. In FIG. 5A there is shown a piston member having a head 13 in which a circumferential groove holds a sealing ring 54. In FIG. 5B a variation of the piston head with sealing ring 54 is shown, further having a flared cup 55. The flared cup provides a strong seal against fluid leakage in the direction opposing the flare. In FIG. 5C is shown a piston member having an integrally-formed head with a frontal flared cup 55, are a spaced-apart rear portion 56, which, because of its thinness, may be of a large diameter and operate as a bidirectional seal and scraper The piston skirt in any of these embodiments preferably has one or more longitudinal ridges, 122 in FIG. 2, arrayed along its exterior surface, to minimize the area of contact with the reservoir wall and to diminish frictional drag.

Turning now to FIG. 6, there is shown an embodiment of the present invention usable as a large volume or macro-pump which may be suspended for bedside use in a vertical orientation in a manner similar to a conventional gravity infusion reservoir. The reservoir and drive assembly of the macro-pump are scaled-up versions of the device of FIG. 1, having a housing 66 which accepts a reservoir 61 having a piston drive member 62. The reservoir is removably attached to the housing as by lip 68 of the reservoir and circumferential groove 69 in the housing, or by a breech lock or similar arrangement. The piston member 62 includes a piston face 63, which may be further sealed using an O-ring or any of the structural variations shown in FIGS. 5A, B or C.

In FIG. 7 is shown a cutaway view along line 7—7 of the embodiment of FIG. 6, in which a motor 35 and drive screw 14 are shown driveably engaging internal threads of piston member 62. FIG. 8 further shows a slot in housing 66 for holding piston drive member 62 in alignment. After insertion of the reservoir assembly into the housing a sliding plate 80 may be moved along axis 88 to close the slot and hold the piston drive member 62 in engagement with screw gear 14. Alternate means for biasing the drive assembly are possible. Furthermore, while FIG. 7 shows a drive shaft journalled in the housing, such housing journals are not necessary, and the drive screw assembly may be simply mounted on the motor shaft, and the motor attached to the housing.

Because of the rigidity of the reservoir and the precise volumetric relationship between drive rotations and piston displacement the macro-pump embodiment is readily adaptable to microprocessor drive control and information display in a manner to yield extremely precise dosage control. This rigid piston and reservoir configuration eliminates the air space characteristic of bottle reservoirs (which consequently require venting, drip chambers, and other equipment) and the undefined volume characteristic of bag reservoirs (which do not permit ready indication delivered fluid volume), achieving in a single apparatus the precision normally associated with separate, expensive, dosing pumps. The housing 66 may house both a microprocessor controller and a battery power supply.

Figure 9:
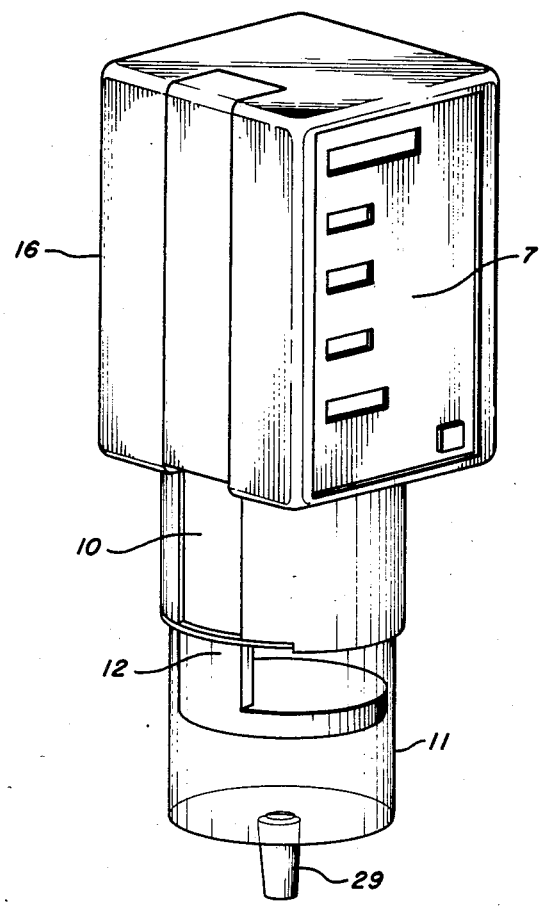
FIG. 9 shows the large volume pump of FIG. 6 including the housing adapted to house a keyboard, control circuitry and power supply.

FIG. 9 shows such a device, in which the housing 16 includes a keyboard 7 on one face, comprising a small number of programming keys. The panel may incorporate a display similar to 9 of FIG. 1, of a kind known in the art, on which may appear messages to guide an attendant in entering the program data related to reservoir volume, total dose and timing. Such a display may also display relevant information such as the total delivered dose, or time interval since last infusion, all of which may be conveniently coded, stored and retrieved starting with the basic operating pulse data of the pump drive and the coded program data of the microprocessor control, by techniques known in the art.

It should be noted that although the foregoing discussion speaks of the fabrication of one embodiment using a motor and reducing gear, it is by no means necessary that the motor be an electromagnetic rotary motor capable of continuous operation. Indeed, a stepping motor, or even a solenoid or piezo ratchet driven motor would be equally serviceable, as long as the device were capable of having its total angular rotation precisely controlled or monitored by the control means. Whereas a continuous duty rotary motor may prove best for conveniently infusing an initial slug of medication, a stepping motor or ratchet drive may prove the most efficient or reliable for sustained infusion of maintenance doses at very low rates. In that event, a solenoid-actuated ratchet gear and corresponding digital control signalling means may be provided in the space shown for the motor. Furthermore, while the piston member has been shown as having a long thin body for simplicity, the relevant structural limitation is that the piston member comprise not much more than about 180° of arc of a cylindrical surface so that it may be conveniently placed in engagement around the drive gear. Thus a plurality of suitably spaced elements with internal threads in registry, or a wider piston member could be employed instead of the single thin piston body shown.

Accordingly, while the invention has been described with reference to specific embodiments thereof, it is to be understood that the invention may be embodied in other forms without departing from the spirit and scope of the invention as defined by the following claims.

What is claimed is:

1. A volumetric pump, comprising:
   reservoir means for providing a reservoir of variable volume, including a piston located within the reservoir means which when axially displaced causes a change in reservoir volume;

drive means in mechanical connection with the piston, for displacing the piston when such means is engaged against a rotating member having a component of angular velocity in the direction of piston displacement, such drive means having an interior drive surface that is substantially a longitudinal section of a surface of revolution about a first axis substantially parallel to the direction of piston displacement, such interior drive surface being threaded for a length at least as great as the desired total piston displacement;

a rotating, axially non-displaceable drive screw which is short in comparison to the displacement of the piston and has an axis or rotation approximately coincident with the first axis, in engagement with the interior drive surface, for displacing the piston;

wherein the reservoir means and drive means form an assembly that is removably engageable against the drive screw; and sever-connection means, for temporarily connecting the piston to the drive means, for movement of the drive means when so connected to the piston both to increase and to decrease the volume of the reservoir means, in such a way that the sever-connection means must be severed to permit placing of the drive means in engagement with the drive screw, and so that following such severence the piston is no longer connected to the drive means and can then be moved only to decrease the volume of the reservoir means.

2. A pump according to claim 1, wherein the sever-connection means includes a stem, one end of which severably connects the piston and the drive means and the other end of which serves as a handle to manipulate displacement of the piston before the stem is severed.

3. A reservoir assembly for removable engagement with a motor drive, comprising:
   a reservoir;
   a piston having (i) a fluid contacting head portion located within the reservoir and (ii) a drive body for engagement with a motor drive and having an aperture therein;
   a severable stem, removably attaching the fluid contacting head portion to the drive body, protruding from the fluid contacting head portion through the aperture in the drive body sufficiently far to prevent the drive body from being engaged with the motr drive without the stem first having been severed, so that when the piston is placed in engagement with the motor drive the head portion is detached from the body and retraction of the head portion and refilling of the reservoir are prevented.

4. A reservoir assembly according to claim 3, wherein the stem extends along a central longitudinal piston axis and blocks the motor drive from engaging an internal surface of the piston.

5. A reservoir assembly according to claim 3, wherein the stem is of sufficient strength to transmit push and pull forces for filling and bleeding the assembly, but has a weak portion which may be severed by twisting, so as to detach the head portion from the body.

6. A reservoir assembly according to claim 5, wherein the stem is integrally formed with the piston head portion.

7. A reservoir assembly according to claim 4, wherein the drive body has affixed thereto a piston follower, threaded along its interior for a length greater than the desired total piston displacement.

* * * * *